United States Patent [19]

Rowlette

[11] Patent Number: 4,499,424
[45] Date of Patent: Feb. 12, 1985

[54] STATE-OF-CHARGE COULOMETER

[75] Inventor: John J. Rowlette, Monrovia, Calif.

[73] Assignee: The United States of America as represented by the Administrator of the National Aeronautics and Space Administration, Washington, D.C.

[21] Appl. No.: 367,136

[22] Filed: Apr. 9, 1982

[51] Int. Cl.³ ............................................ G01N 27/46
[52] U.S. Cl. ...................................... 324/427; 429/58
[58] Field of Search ............... 324/425, 426, 427, 428, 324/434, 430; 320/39, 48; 429/58, 61, 90, 91

[56] References Cited

U.S. PATENT DOCUMENTS

| | | | |
|---|---|---|---|
| 3,680,072 | 7/1972 | Charbonnier et al. | 340/249 |
| 3,890,556 | 6/1975 | Melling et al. | 320/21 |
| 3,901,729 | 8/1975 | Duddy | 429/61 |
| 3,946,299 | 3/1976 | Christianson et al. | 320/43 |
| 3,984,762 | 10/1976 | Dowgiallo, Jr. | 324/29.5 |
| 4,080,560 | 3/1978 | Abert | 324/29.5 |
| 4,207,514 | 6/1980 | Klein | 320/44 |

Primary Examiner—Michael J. Tokar
Assistant Examiner—Kevin D. O'Shea
Attorney, Agent, or Firm—Paul F. McCaul; John R. Manning; Thomas H. Jones

[57] ABSTRACT

A coulometer for accurately measuring the state-of-charge of an open-cell battery utilizing an aqueous electrolyte. The coulometer includes a current meter (38) for measuring the battery charge/discharge current and a flow meter (42) for measuring the rate at which the battery produces gas during charge and discharge. Coupled to the flow meter is gas analyzer (54) which measures the oxygen fraction of the battery gas. The outputs of the current meter, flow meter and gas analyzer are coupled to a programmed microcomputer which includes a CPU (68) and program and data memories (74), (76). The microcomputer calculates that fraction of charge and discharge current consumed in the generation of gas so that the actual state-of-charge can be determined. The state-of-charge is then shown on a visual display (80).

15 Claims, 11 Drawing Figures

CHARGE PROFILE A

CHARGE PROFILE B

CHARGE PROFILE C

|  | PROFILE A | PROFILE B | PROFILE C |
|---|---|---|---|
| PROCEDURE 1 | $I_c$ = 25 AMPS<br>$V_c$ = 7.2 VOLTS | $I_c$ = 25 AMPS<br>$V_s$ = 7.8 VOLTS<br>$V_c$ = 7.2 VOLTS | $I_{c1}$ = 25 AMPS<br>$V_s$ = 7.8 VOLTS<br>$I_{c2}$ = 5 AMPS |
| PROCEDURE 2 | $I_c$ = 25 AMPS<br>$V_c$ = 7.8 VOLTS | $I_c$ = 30 AMPS<br>$V_s$ = 7.8 VOLTS<br>$V_c$ = 7.2 VOLTS | $I_{c1}$ = 25 AMPS<br>$V_s$ = 7.8 VOLTS<br>$I_{c2}$ = 10 AMPS |
| PROCEDURE 3 | $I_c$ = 25 AMPS<br>$V_c$ = 8.0 VOLTS | $I_c$ = 25 AMPS<br>$V_s$ = 8.0 VOLTS<br>$V_c$ = 7.2 VOLTS | $I_{c1}$ = 25 AMPS<br>$V_s$ = 7.2 VOLTS<br>$I_{c2}$ = 5 AMPS |

CHARGE PROFILES & PROCEDURES

FIG. 2

STATE OF CHARGE (AMPERE-HOURS)
(POSITIVE ELECTRODE — ○)
(NEGATIVE ELECTRODE — △)

| NO. OF ERRORS LESS THAN 1% | 19% |
| --- | --- |
| NO. OF ERRORS LESS THAN 5% | 71% |
| NO. OF ERRORS LESS THAN 10% | 87% |
| MAXIMUM POSITIVE ERROR | +30.4% |
| MAXIMUM NEGATIVE ERROR | -15.0% |
| PERCENT POSITIVE ERRORS | 48.4% |
| PERCENT NEGATIVE ERRORS | 51.6% |

ANALYSIS OF ERRORS FOR STATE-OF-CHARGE INDICATION

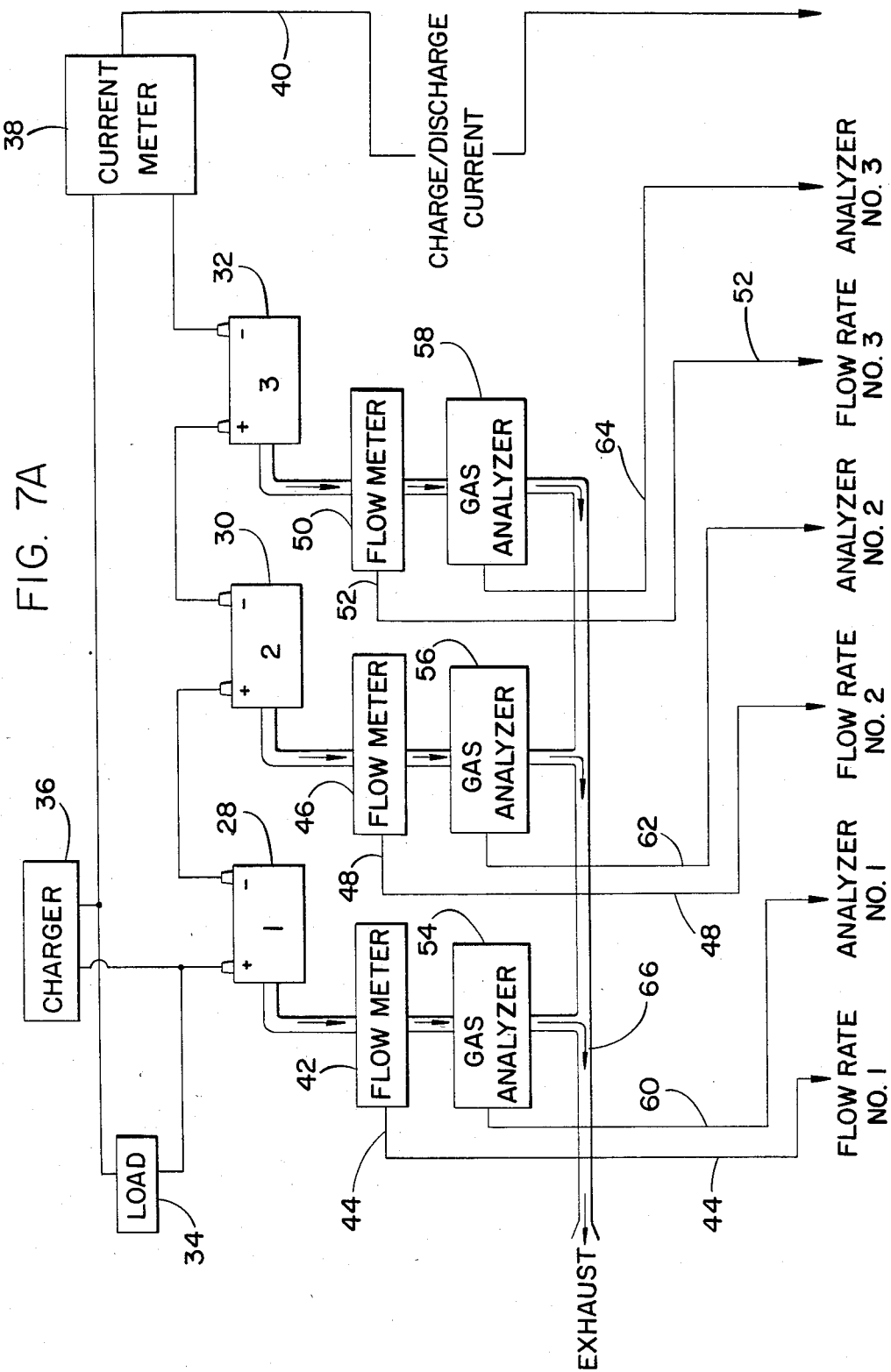

STATE-OF-CHARGE COULOMETER

1. ORIGIN OF THE INVENTION

The invention described herein was made in the performance of work under a NASA Contract and is subject to the provisions of Section 305 of the National Aeronautics and Space Act of 1958, Public Law 85-568 (72 STAT 435; 43 USC 2457).

2. TECHNICAL FIELD

The subject invention pertains to the field of coulometers, and more particularly, to battery state-of-charge coulometers.

3. BACKGROUND ART

An accurate knowledge of the state-of-charge of a cell or battery is often needed. For example, it is of critical importance that the state-of-charge of the batteries of an electric-powered vehicle be precisely known.

The fuel gauge of an internal combustion engine-powered automobile is a very useful instrument. Such an instrument permits a driver to estimate the remaining range based upon the amount of fuel in the fuel tank. The state-of-charge of the batteries of an electric-powered vehicle is analogous to the amount of fuel in the fuel tank and representative available number of ampere-hours which can be delivered by the batteries under specified conditions.

If a gasoline-powered automobile runs out of fuel, the driver will obviously be inconvenienced. However, a small quantity of fuel can be added to the tank so that the automobile may be driven to the nearest gasoline station for quick refueling. A stranded electric-powered vehicle presents a much more serious problem. Battery recharging equipment is very difficult to transport; therefore it would be impracticable under most circumstances to give a recharge to a stranded electric-powered vehicle. The vehicle would most likely have to be towed to the nearest recharging facility for a time-consuming recharge.

State-of-charge coulometers for electric-powered vehicles are notoriously inaccurate. In order to avoid becoming stranded, drivers add a considerable safety margin to the estimated state-of-charge. Thus, the effective range of an already range-limited vehicle is further reduced.

The state-of-charge of a battery is a function of many variables. The most important variables are obviously the quantity of charge (ampere-hours) added during charging and the quantity of charge taken out during discharge. These two variables can be readily determined using prior art integrating ammeters which are otherwise known as coulometers.

Unfortunately, the total quantity of the charge added during charging cannot be recovered during discharge. Stated differently, under most typical operating conditions, the coulombic efficiency (as opposed to energy efficiency) of a battery is less than 100 percent. There are inefficiencies during both the charge and the discharge cycles. Charge efficiency, which is usually more significant than discharge efficiency, is a function of charge voltage, charge current, battery temperature, battery age and other variables. Discharge efficiency is a function primarily of the discharge current, although other variables have an influence. However, there are no substantial coulombic inefficiencies in a lead/acid battery at normal discharge rates.

Prior art coulometers do not effectively take into account the major sources of coulometric inefficiencies of batteries. Accordingly, such devices are unsatisfactory for use in electric-powered vehicles and similar applications. The coulometer disclosed herein overcomes these limitations of the prior art device and is capable of accurately measuring the state-of-charge of a battery. These and other advantages of the subject device will become apparent upon reading of the following disclosure in conjunction with the drawings.

4. DISCLOSURE OF THE INVENTION

A coulometer for measuring the state-of-charge of an electrolytic cell utilizing an aqueous electrolyte is disclosed. The coulometer includes a current measuring means, such as a current meter, for measuring the cell charge and discharge current. Gas flow measurement rate apparatus is provided which is coupled to the cell gas vent which measures the rate of gas generation of the cell.

The outputs of the current measuring apparatus and gas flow apparatus are coupled to the interface of a suitably programmed microprocessor. The microprocessor calculates the efficiency of the cell based upon the rate at which the cell generates gas. Given the overall efficiency of the cell, and the magnitude of the total current flow through the cell, the microprocessor computes the true state-of-charge.

5. BRIEF DESCRIPTION OF THE DRAWINGS

FIG. 2 is a table showing the various magnitudes of the current and voltages for the charge profiles of FIGS. 1A–1C.

Figures 5, 6:
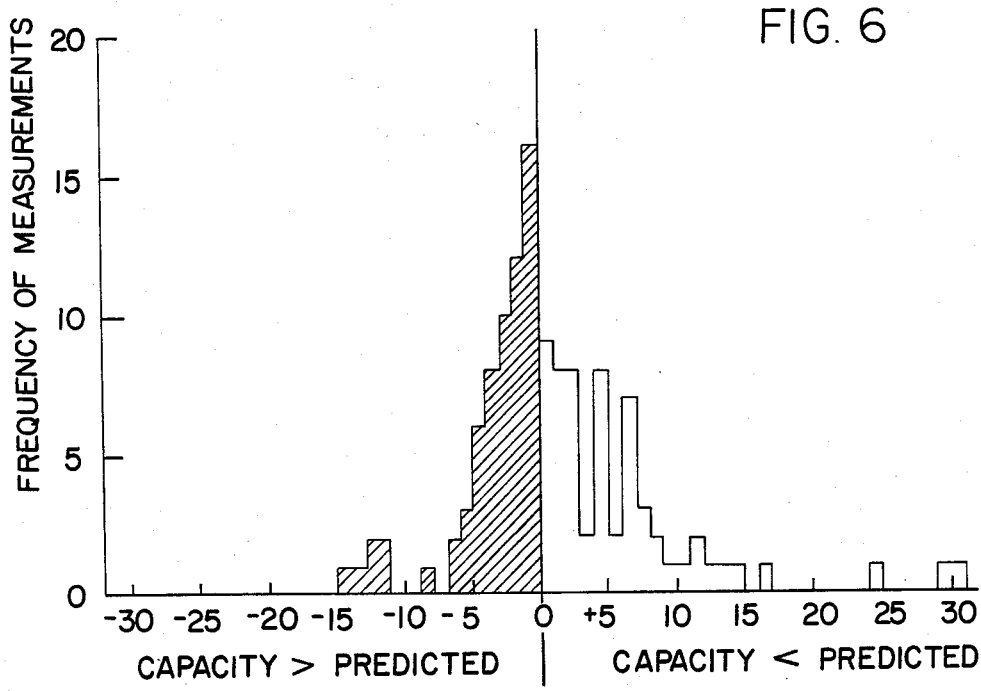

FIG. 5. is a table showing an analysis of the errors of the FIG. 6 bar graph.

FIG. 6 is a bar graph which represents the accuracy of the test results in predicting battery capacity.

Figure 7B:
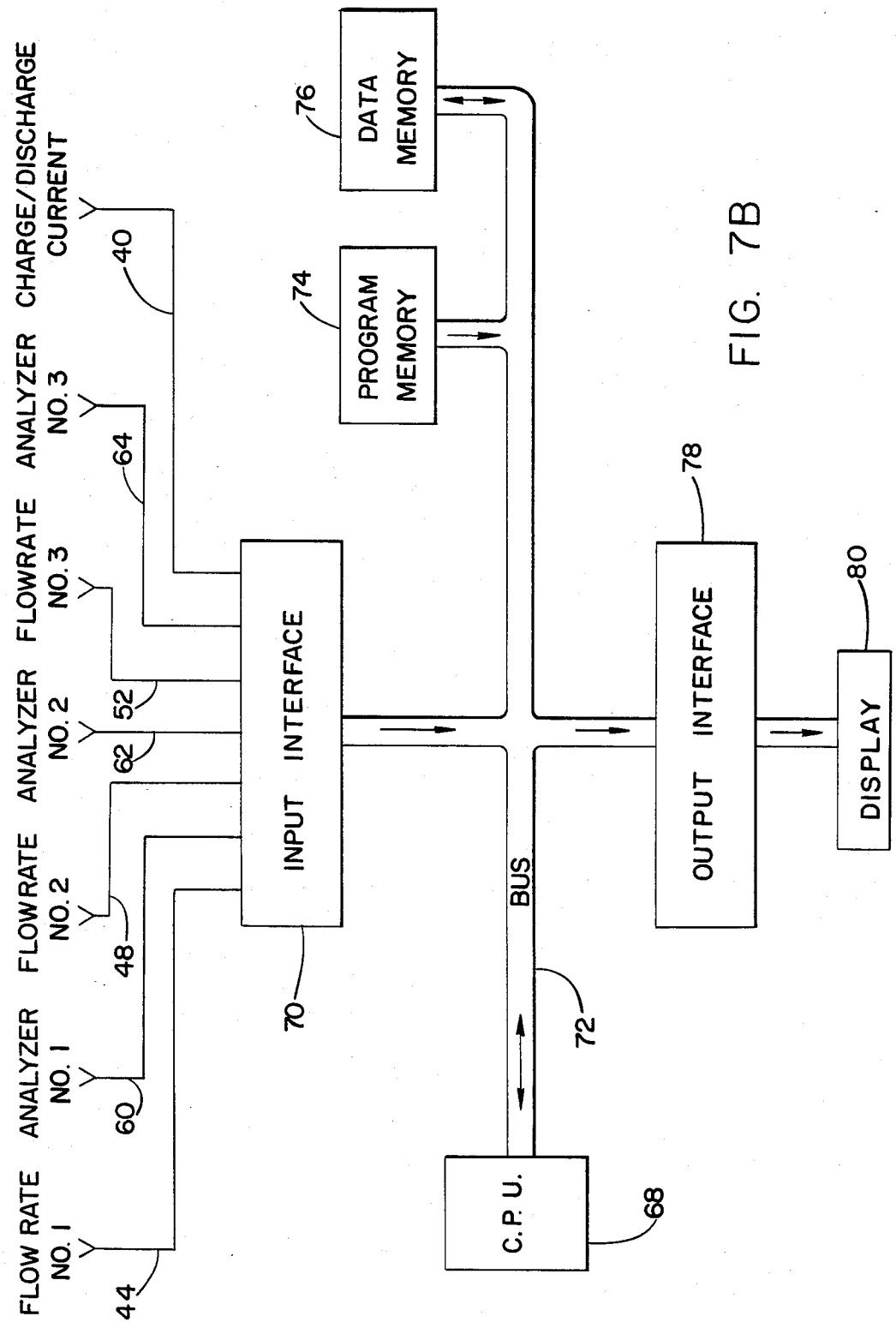

FIGS. 7A–7B represent a simplified block diagram of the subject invention.

Figure 8:
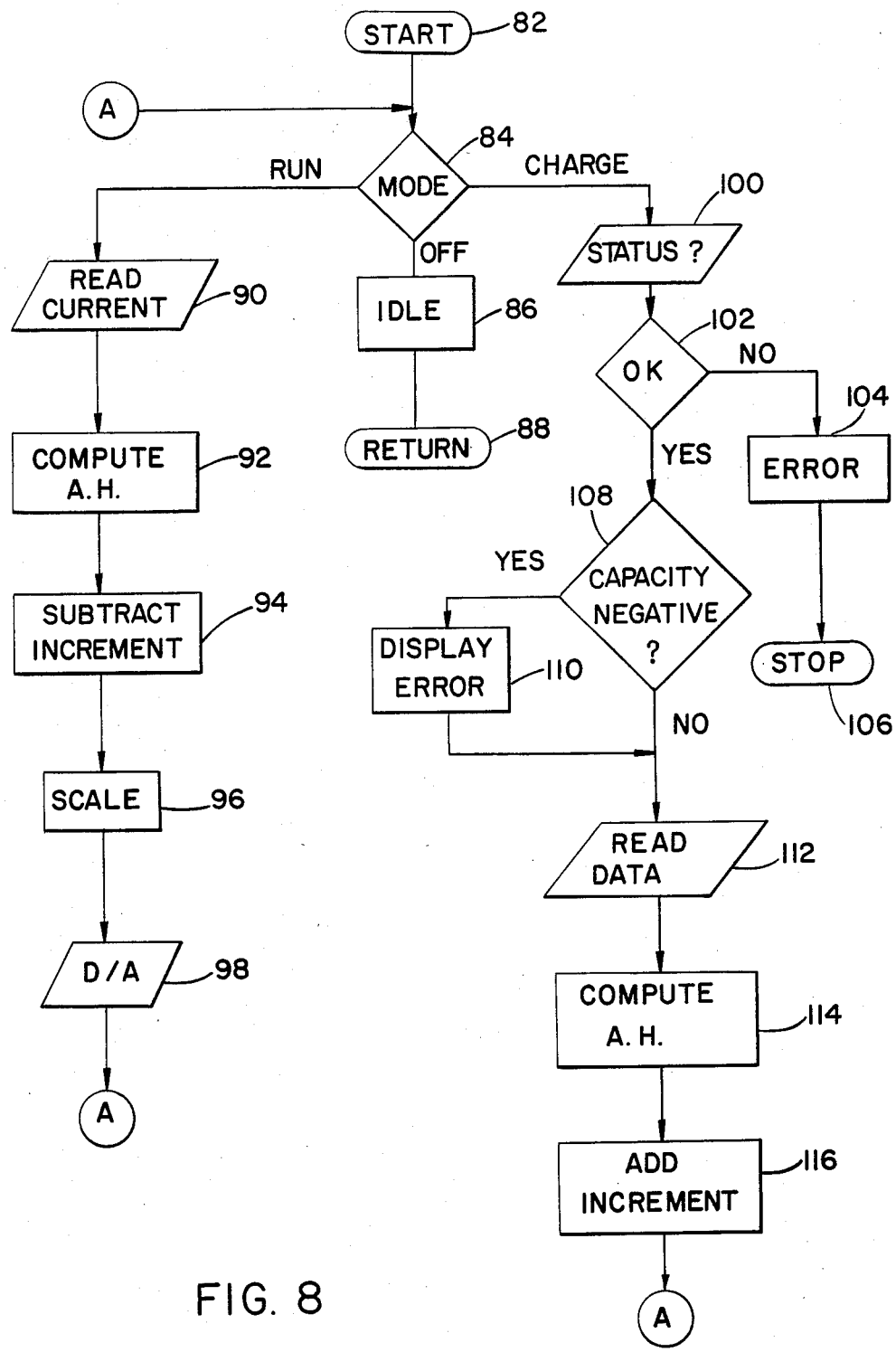

FIG. 8 is a simplified flow chart for an exemplary computer program to be used in the apparatus of FIGS. 7A–7B.

6. BEST MODE FOR CARRYING OUT THE INVENTION

It is likely that electric vehicles in the near future will be powered primarily by lead-acid batteries. When a lead-acid cell is being charged, substantially all of the charging current goes into one or both of two electrochemical processes occurring at each of the electrodes. With respect to the positive electrode, lead dioxide is produced and/or oxygen is generated during the charging process. Oxygen will also be generated at this electrode in the discharge cycle, especially if the rate of discharge is high. Similarly, lead is produced and/or hydrogen is generated at the negative electrode during the charge cycle.

The production of hydrogen and oxygen is common to all electrolytic cells utilized an aqueous electrolyte. These side or parasitic reactions are the primary source of coulometric inefficiency of such batteries.

The electrolysis reaction may be expressed as follows:

$$H_2O \rightarrow H_2 + \tfrac{1}{2}O_2 \qquad (1)$$

Equation (1) above, is the sum of the following two half-cell reactions:

$$H_2O \rightarrow \tfrac{1}{2}O_2 + 2H^+ + 2e^- \qquad (2)$$

and $$2H^+ + 2e^- \rightarrow H_2 \qquad (3)$$

From Equation (1) above, it can be seen that for the passage of two equivalents (Faradays) of electricity, one mole of hydrogen and one half a mole of oxygen are evolved. Since a Faraday is equivalent to 96,487.3 coulombs, which is expressed in ampere-seconds, one equivalent of a chemical reaction is equal to 96,487.3 ampere-seconds divided by 3,600 seconds/hour or 26.802 ampere-hours.

As can be seen from Equation (2) above, one equivalent of electricity results in $\tfrac{1}{4}$ mole of oxygen. Similarly, Equation (3) shows that one equivalent of electricity results in $\tfrac{1}{2}$ mole of hydrogen. Measured at standard temperature and pressure (0° C. and 1 atm.), $\tfrac{1}{4}$ mole of oxygen has a volume of 5,603 cm³ and $\tfrac{1}{2}$ mole of hydrogen has a volume of 11,206 cm³. Thus, it can be readily calculated that one ampere of current will produce an oxygen flow rate as follows:

$$1 \text{ ampere} = 3.482 \text{ cm}^3/\text{min of } O_2 \text{ @ STP} \qquad (4)$$

Similarly, one ampere of current will produce a hydrogen flow rate as follows:

$$1 \text{ ampere} = 6.965 \text{ cm}^3/\text{min of } H_2 \text{ @ STP} \qquad (5)$$

Equation (4) above represents the amount of current at the positive electrode which is consumed in the generation of oxygen. This current does not contribute to the state-of-charge of the battery during the charge cycle and does not contribute to the discharge current during the discharge cycle. Similarly, Equation (5) represents the amount of current at the negative electrode which is consumed in the generation of hydrogen. This current also does not contribute to the state-of-charge of the battery during the charge cycle and does not contribute to the discharge current during discharge.

It was hypothesized that the charge and discharge inefficiencies of aqueous electrolyte batteries could be determined by measuring the rate of gas flow produced by the parasitic reaction occurring at the positive and/or negative electrodes. Thus, charge and discharge inefficiences could be readily determined using Equations (4) and (5) above. By taking into account charge and discharge inefficiencies, the state-of-charge of such batteries could be accurately determined.

In order to verify the above hypothesis, a series of tests were conducted on six lead-acid batteries. The batteries are manufactured and sold by ESB, Inc. of Horsham, Pa. under the trademark "EV-106." Three of the batteries were tested in "new" condition. The "new" batteries were preconditioned by subjecting them to three charge and discharge cycles. The remaining three batteries were tested in an "aged" condition. The batteries were "aged" by subjecting them to a total of two hundred deep charge and discharge cycles over an extended period of time.

The six batteries were then subjected to a series of tests. The pertinent portion of the test method generally comprised the steps of fully charging the batteries using various charging procedures and then discharging the batteries in accordance with a common discharge procedure. Battery charging took place at three temperatures, namely, 0°, 20° and 49° C. During the charging cycle, battery voltage, battery current, gas flow and other measurements were recorded. Next, the batteries were discharged using a single discharge procedure. Finally, a comparison was made between the predicted state-of-charge of the batteries and the actual state-of-charge.

Figure 1A:
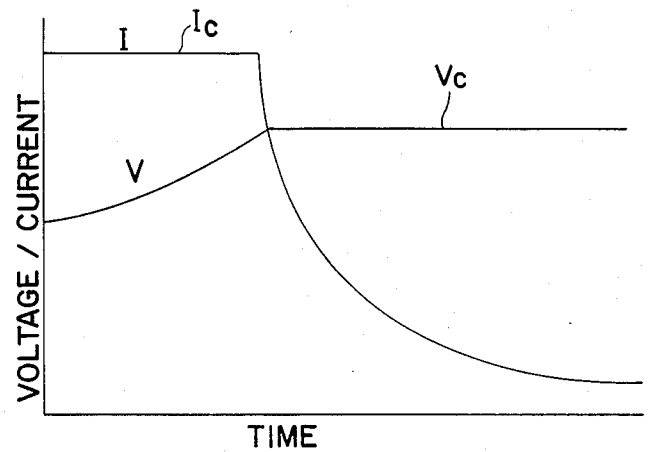
FIGS. 1A–1C are charge profile curves illustrating the manner in which batteries under test were charged.
Figure 1B:
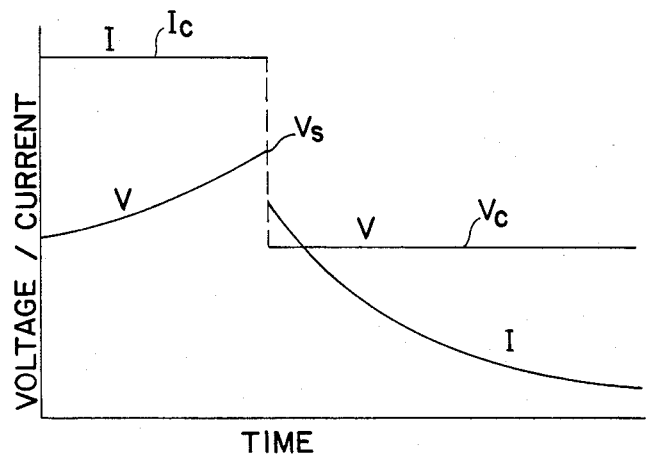
Figure 1C:
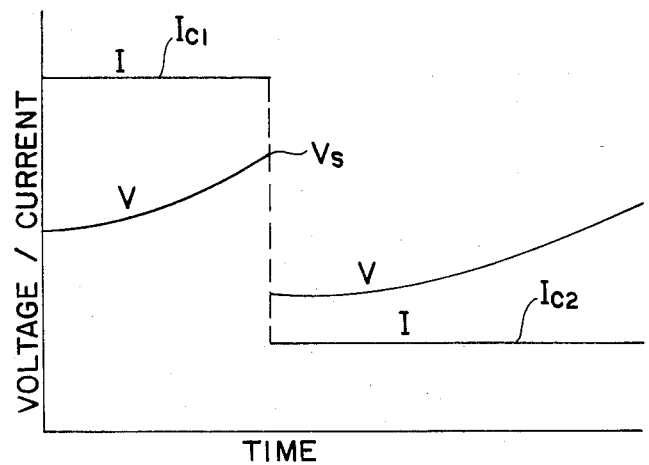

Referring now to the drawings, FIGS. 1A–1C show the three charging profiles which were used for charging the test batteries. As can be seen in FIG. 1A, charge profile A requires that the battery be initially charged at a constant current Ic until a preselected voltage Vc is reached. Once voltage Vc is reached, the voltage is clamped at that value until the battery is fully charged.

The second charging profile, profile B, is shown in FIG. 1B. The charge is commenced by maintaining a constant charging current Ic until a predetermined voltage Vs is reached. At that time, the charging voltage is reduced from Vs to a clamped voltage Vc until the battery is fully charged.

The third charging profile, profile C, is shown in FIG. 1C. Charging is initiated by applying a constant current $I_{c1}$. This current is maintained until the battery voltage reaches a predetermined value $V_s$. Once $V_s$ is reached, charging continues at a lower constant current level $I_{c2}$ until the battery is fully charged.

The values of $I_c$, $I_{c1}$, $I_{c2}$, $V_s$ and $V_c$ were varied for each charge profile. For purposes of convenience, a set of these values is referred to herein as a "charge procedure." Three charge procedures were conducted for each charge profile. FIG. 2 shows the values of $I_c$, $I_{c1}$, $I_{c2}$, $V_s$, and $V_c$ for the various charge procedures. For example, charge procedure 1 for charge profile B utilizes the following values:

$I_c = 25$ amps;

$V_s = 7.8$ volts; and $V_c = 7.2$ volts.

The discharge procedure was the same for all tests. The fully charged batteries were discharged at a constant current of 50 amperes until the voltage was reduced to 3.9 volts. Discharge took place at 20° C.; therefore, batteries with charging temperatures other than 20° C. were soaked at temperature for 24 hours.

Charge and discharge data were recorded with the aid of a suitably programmed minicomputer. Battery voltage was measured and recorded at the beginning of the charge and discharge cycle. The voltage was also recorded every 30 seconds and after every 20 mv change in battery voltage. Charge and discharge current was measured and recorded coincident with voltage movement.

Figure 3:
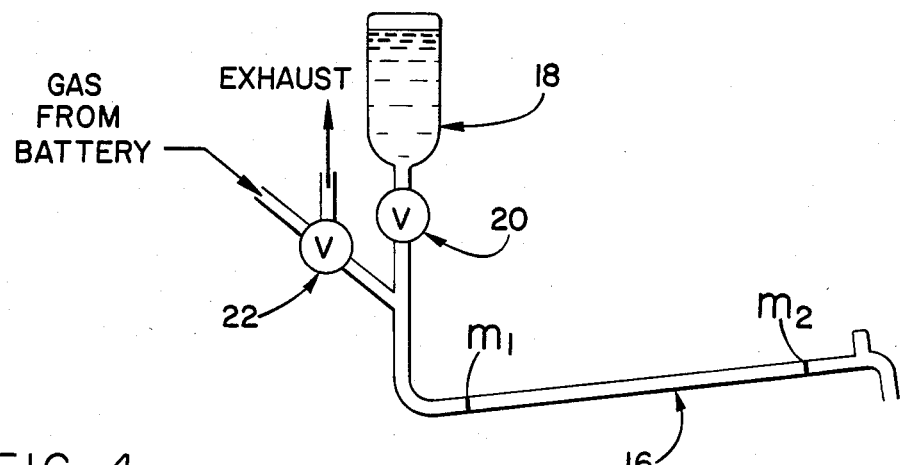
FIG. 3 is a schematic representation of an apparatus used to measure the rate of gas flow of the batteries under test.

Total gas flow rates were determined and recorded manually every half hour during the charge cycle. This measurement was made with the aid of a positive displacement apparatus as can be seen in FIG. 3. The apparatus is comprised of a transparent measuring tube 16 which is positioned at a slight angle to horizontal. Tube 16 is provided with a first indicating mark M1 located at its lower end and a second indicating mark M2 located at its upper end. The upper end of tube 16 is open, with the lower end being coupled to a water reservoir 18 outlet through an on/off valve 20. Tube 16 is also coupled to a manifold (not shown) which carries the gases evolving from the battery under test by way of two-way valve 22. The two-way valve 22 can be switched to a second (normal) position wherein the battery gases are shunted to an exhaust.

The apparatus is initially calibrated by measuring the volume of tube 16 between markers M1 and M2. Next, valve 20 is opened to allow water from reservoir 18 to enter measurement tube 16. Only a small amount of water sufficient to create a meniscus need be introduced. Two-way valve 22 is then switched out of the normal position so as to permit battery gas to enter measurement tube 16. As the gas enters tube 16, the water located in the lower portion of the tube is driven from the lower portion of the tube, past marker M1 to the upper portion. The time required for the trailing miniscus to travel from marker M1 to marker M2 is measured using a stopwatch or the like. At the end of the measurement, valve 22 is turned back to the normal position so that the battery gas is free to exhaust.

The total gas flow rate can then be determined based upon the known volume of tube 16 between markers M1 and M2 and the time measurement. Given the relatively low mass of the water entrapped in the measurement tube 16 and the slight angle of the tube, very little back pressure will be created by the measurement apparatus. Accordingly, the apparatus will have little tendency to affect the rate of gas flow.

The oxygen flow rates were determined from the total gas flow rates and the oxygen concentration in the gas stream. The latter was measured using a conventional oxygen analyzer such as manufactured by Beckman Instruments. The hydrogen flow rates were determined by the differences between the total flow rates and oxygen flow rates.

A total of 124 tests were performed on the new and aged batteries. The tests were performed using various combinations of charging profiles and procedures at the three temperature levels. In some tests, the batteries were only partially charged. In addition, tests were performed with single batteries and batteries connected in series.

Figure 4:
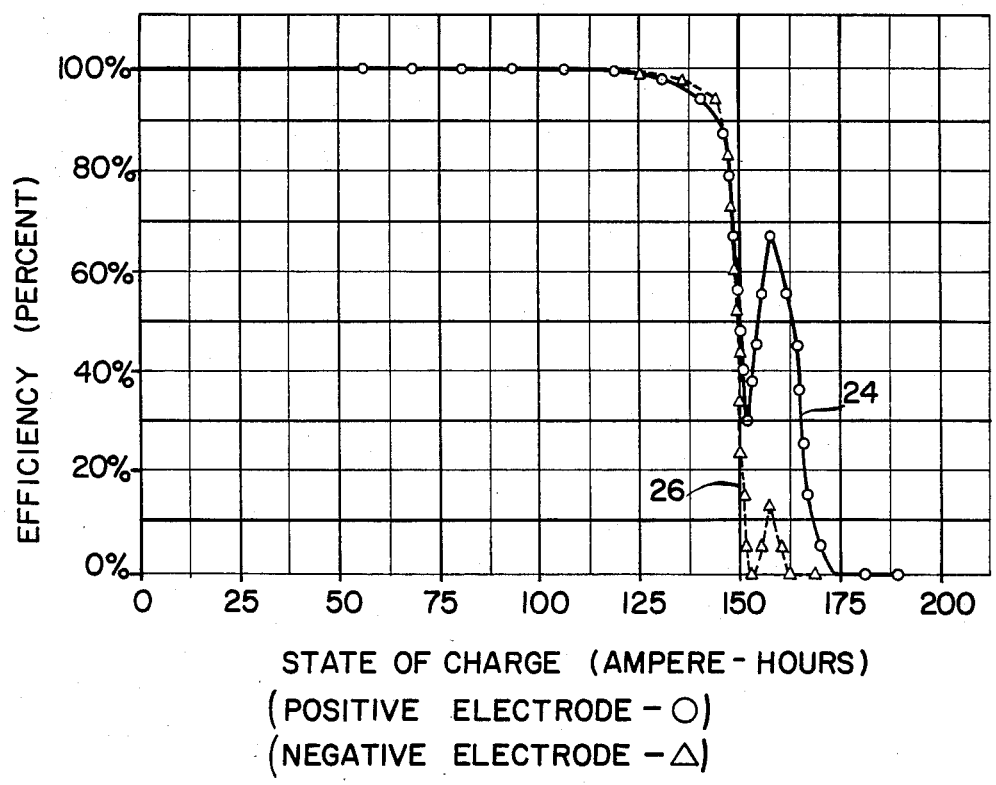
FIG. 4 is an exemplary graph showing the charge efficiency of the positive and negative electrodes of a battery under test.

FIG. 4 shows a set of curves which was produced from the data taken during a typical test. A single new battery was tested at 20° C. The battery was charged in accordance with charge profile A and charge procedure 2. Thus, as can be seen in FIGS. 1A and 2, the battery was initially charged at a constant current $I_c$ of 25 Amperes. The battery was permitted to charge at this rate until the terminal voltage reached 7.8 volts. At this point, the voltage was clamped at 7.8 volts ($V_c$) until the battery was overcharged.

Curves 24 and 26 of FIG. 4 represent the charge efficiency versus state-of-charge of the positive and negative electrodes of the battery, respectively. The charge efficiency of the positive electrode was determined by the rate of oxygen evolution in accordance with Equation 4. Similarly, the charge efficiency of the negative electrode was determined by the rate of hydrogen evolution in accordance with Equation 5. The overall efficiency is determined by the least efficient electrode.

As can be seen from curves 24 and 26, the efficiency of both electrodes is 100 percent for relatively low states of battery charge. This optimum efficiency is established by the fact that the flow rate of oxygen and hydrogen gas was measured to be practically zero. Thus, substantially all of the charging current was being devoted to increasing the state-of-charge of the battery under test rather than generating gas.

At a state-of-charge of roughly 100 ampere-hours, the battery began producing gas. The gas initially produced was primarily oxygen thereby indicating that the efficiency of the positive electrode was dropping off. At about 130 ampere-hours, significant quantitites of hydrogen were also being measured. At that point, the efficiency of both electrodes was reduced to roughly 94 percent as indicated by curves 24 and 26.

At a state-of-charge of approximately 153 ampere-hours, the efficiency of the negative electrode dropped to 0 percent. Thus, the entire charging current at the negative electrode was devoted to the production of hydrogen. At the same state-of-charge, the efficiency of the positive electrode had decreased to approximately 30 percent.

The efficiency of both electrodes increased substantially at roughly 156 ampere-hours. At approximately 170 ampere-hours, the efficiency of both electrodes dropped to 0 percent. Thus, the battery was fully charged and essentially all of the charging current was expended in the production of hydrogen and oxygen.

The fully charged battery was then discharged in order to determine the accuracy of the predicted state-of-charge. At very high discharge rates, the discharge efficiency is less than 100 percent. Such discharge efficiency can be determined in the same manner as the charge efficiency based upon the rate of oxygen evolution and applying Equation 4. However, at relatively low discharge rates, the discharge efficiency is effectively 100 percent. For the relatively low discharge rate of 50 amperes, it was assumed that the discharge efficiency was 100 percent.

A comparison between the predicted state-of-charge and the actual state-of-charge revealed that the rate of battery gas evolution provided an accurate means for determining the true state of battery charge. FIGS. 5 and 6 show a summary of an error analysis performed on the results of the 124 tests. As can be seen from FIG. 5, almost 90 percent of the predicted state-of-charge measurements were within 10 percent accuracy. The error distribution diagram shown in FIG. 6 reveals that the errors were fairly evenly distributed. Approximately 48 percent of the errors were the results of over-prediction of battery capacity and approximately 52 percent were for under-prediction of capacity.

There were a few relatively large errors in prediction of capacity. However, most of these errors could be accounted for. The largest error was a 30.4 percent over-prediction of capacity. The battery tested was one of three aged batteries connected in series. The two other batteries had positive errors of only 6.7 and 6.6 percent. It appeared that these two batteries were stronger than the third and drove the battery in reverse thereby causing the large over-prediction.

It is likely that the remainder of the larger errors were the result of inaccurate gas flow rate measurements taken at the higher flow rates. Near the end of charge, the gas flow rates were such that time measurements of less than one second were required. It is very possible that these short time periods were not accurately measured by the stopwatch.

FIGS. 7A and 7B show a simplified block diagram of an exemplary battery installation utilizing the subject invention. The installation utilizes three open-cell lead-/acid batteries 28, 30 and 32. The three batteries are connected in series to a load 34 which may be, for example, the electric motor of an electric-powered vehicle. Also connected across batteries 28, 30 and 32 is a conventional battery charger 36. Charger 36 is typically connected to a stationary electrical power source (not shown).

A conventional digital current meter 38 is connected in series within the negative electrode of battery 32. Meter 38 provides an output on line 40 indicative of the magnitude of both the charge current and the discharge current.

A separate gas flow meter is connected to the gas vent output of each of the batteries. Flow meter 42 is coupled to the vent of battery 28. The flow meter provides an output on line 44 indicative of the total rate of gas flow evolving from battery 28. Similarly, flow meters 46 and 50 are coupled to the vents of batteries 30 and 32, respectively. Flow meters 46 and 50 provide outputs on lines 48 and 52, respectively.

The output of each of the flow meters is coupled to a conventional gas analyzer. The analyzers are preferably oxygen analyzers although hydrogen analyzers can also be used. The analyzers provide an output signal indicative of the percentage of oxygen (or hydrogen) present in the gas stream. The output of flow meter 42 is coupled to an analyzer 54 which provides an output signal on line 60. Similarly, the outputs of flow meters 46 and 50 are coupled to analyzers 56 and 58, respectively, such analyzers providing output signals on lines 62 and 64, respectively.

The gas output of each of analyzer is coupled to a common manifold 66. Manifold 66 carries the potentially explosive gases to a common exhaust.

Referring now to FIG. 7B, the remainder of the simplified block diagram may be seen. The various output signals are processed by a central processing unit (CPU) 68. CPU 68, which can be one of many well known integrated circuit microprocessor chips such as the Intel model 8080, is coupled to an input interface 70 by way of a system bus 72. The input interface 70 receives the various outputs of current meter 38 on line 40, flow rate meters 44, 46 and 50 on lines 44, 48 and 52, respectively, and gas analyzers 54, 56 and 58 on lines 60, 62 and 64, respectively.

Input interface 70 accomplishes a variety of well known functions. By way of example, the interface 70 converts any analog signals on the input lines to digital signals.

The system bus 72 is also coupled to a program memory 74 and data memory 76. Program memory 76 is preferably a programmable read-only-memory (PROM) which contains the computer program to be subsequently described. Data memory 76 is preferably a random-access-memory (RAM) which stores the program data, including data from input interface 70 and data from CPU 68.

The input of a conventional output interface circuit 78 is also coupled to bus 72. The output of interface 78 is in turn coupled to a display 80. The primary function of interface 78 is to receive data from the data memory 76 and to drive the display. Display 80 can be a conventional analog display similar to fuel gauges now used on gasoline powered vehicles. Digital displays such as light-emitting diodes (LED) or liquid crystal displays (LCD) could also be used.

The computer program stored in program memory is straightforward and can be written by programmers having ordinary skill in the computer programming art. In order not to obscure the true nature of the invention in unnecessary detail, the program will be described only in reference to a simplified block diagram. Referring to FIG. 8, a simplified block diagram of an exemplary program may be seen. It is to be understood that other programs would also be suitable for carrying out the claimed invention.

The program sequence begins at block 82 and advances to block 84. At block 84 a determination is made as to the status of the apparatus. The status would typically be controlled by a three-position switch (not shown) mounted on the vehicle control panel. This switch would be used to place the vehicle in either a "Run," "Charge" or "Off" mode. The microprocessor and associated circuitry will remain powered in all three modes.

If the apparatus is in the "Off" mode, the program will advance to block 86, which is an idle loop. The program will then advance to block 88 and return to the start block 82. The program will remain in the idle loop as long as the apparatus is in the "Off" mode.

When the vehicle is to be driven, the mode switch is thrown to the "Run" mode. The program will then exit the idle loop and advance to block 90. At block 90, the magnitude of the discharge current as determined by current meter 38 (FIG. 7A) is measured. The incremental time lapse since the previous current measurement is also computed. Next, the program advances to block 92 at which time the incremental decrease in ampere-hours is computed. It is assumed that the discharge efficiency is 100 percent.

The program then advances to block 94 at which time the incremental decrease in ampere-hours is subtracted from the current state-of-charge of the batteries which is stored in the data memory 76 (FIG. 7B). The current state-of-charge is then scaled at block 96. For example, if the state-of-charge is one-half of the total capacity of the batteries, a digital signal representing one-half the maxaimum value will be produced.

The program then proceeds to block 98 at which time the scaled digital value is converted to an analog signal. The analog signal is then presented to the display 80 (FIG. 7B).

The program returns to block 84 and then to block 90 if the apparatus is still in the Run mode. At block 90 the magnitude of the discharge current is measured again and the incremental loss in charge is computed based upon the time lapse since the last current measurement. The time between measurements should be on the order of 1 ms. or less to ensure that the total discharge is accurately measured. The total state-of-charge is reduced by the value of the incremental discharge and the current state-of-charge is displayed as previously described.

If the batteries are to be charged, the mode switch is placed in the "Charge" position. The Charge mode is detected at block 84 thereby causing the program to proceed to block 100. At block 100 a determination is made as to state of the charge circuit in order to ensure safe operation. By way of example, a test can be performed to verify that the charger output has been properly connected to the vehicle and that the charger output voltage falls within certain predetermined limits. Other similar status conditions can be monitored if desired.

If the charger status is not proper, the program will advance to block 102 and then to block 104. The program will then enter into an error procedure wherein an error message will be caused to appear on display 80 indicating the nature of the charger error. The program will then proceed to block 106 at which time the program will proceed no further until the error is eliminated by the operator.

Assuming that the charger status is proper, the program will advance to block 108 at which time a determination is made as to the polarity of the present state-of-charge or capacity of each of the batteries is determined. A negative state-of-charge indicates that a battery is defective. If one or more of the batteries has a negative state-of-charge, the program will proceed to block 110 at which time an error message will be caused to be displayed indicating which batteries are defective. The program will not continue further until the apparatus receives a response from the operator to proceed.

If the capacity of each of the batteries is positive, the program will proceed to block 112. At this state, the magnitude of the charging current is measured by way of current meter 38 (FIG. 7A). In addition, the total gas flow rate of each of the batteries is measured by way of flow rate meters 44, 48 and 52 and the oxygen fraction is measured by way of gas analyzers 54, 56 and 58 (FIG. 7A).

The program will then proceed to block 114 at which time the total charge during the incremental time period is calculated. In addition, the amount of charge lost through the generation of hydrogen and oxygen gas is calculated using Equations 4 and 5. Finally, the net incremental increases in charge is calculated by subtracting the charge consumed in the parasitic reactions from the total incremental charge.

The program will then proceed to block 116 at which time the incremental increase in charge is added to the curent state-of-charge value stored in the data memory 76. The current state-of-charge will then be shown on display 80, and the program will return to start block 82. The process will be repeated until the apparatus is switched out of the Charge mode. Once the batteries are fully charged, it is preferable that the some means for automatically shutting off the charger be provided so as to conserve electrical energy.

In order to offset accumulated errors which will result after several charge/discharge cycles, it is necessary to periodically initialize or reset the subject apparatus. One method of initializing is to fully discharge the batteries and set the current state-of-charge value stored in the data memory to zero. Another method would be to fully charge the batteries and set the current state-of-charge value to the maximum value. A full state-of-charge can be determined by, among other methods, monitoring the gas flow rates until the charge efficiency drops to zero percent.

Thus, a novel state-of-charge coulometer has been disclosed. Although an exemplary embodiment has been disclosed in detail, changes may be made by those skilled in the art which would fall within the scope of the subject invention as defined in the appended claims. By way of example, the apparatus could be simplified at the cost of accuracy by eliminating the use of gas analyzers. In that event, the rate of gas generation would be measured and the composition of the gas estimated based upon battery history, battery type and other similar factors. By way of further example, it would be possible to increase the accuracy of the subject apparatus by monitoring the gas evolution during the discharge cycle so that any discharging inefficiencies could be taken into account. In addition, the apparatus could be simplified by measuring the total oxygen and hydrogen flow rates utilizing a single gas flow rate meter and gas analyzer. One disadvantage of this approach is that individual battery failures could not be readily detected. Another approach would be to use a single flow meter and analyzer which periodically samples the gas output of each of the batteries one at a time. This could be accomplished using a manifold having electrically actuated valves which would be under program control. Such valves would sequentially couple the gas output of the batteries to the flow meter and analyzer so that the efficiency of each battery could be individually measured. Individual battery failures could then be detected utilizing this time multiplexing approach. In addition, it may be preferable to incorporate the disclosed coulometer into the charging station itself so that several vehicles can be serviced by a single device. Once a charge was completed, a message would be transmitted to the vehicle indicating the magnitude of the added charge.

What is claimed is:

1. A coulometer for measuring the state-of-charge of an electrolytic cell having an aqueous electrolyte, said coulometer comprising:

current measuring means for producing a total current signal indicative of the amount of current flow through the cell;

gas measuring means for producing a total gas flow rate signal and at least one component gas signal indicative of the rate of generation of oxygen by the cell;

computing means responsive to said total current signal, said total gas flow rate signal and said component gas signal for producing a state-of-charge signal indicative of the state-of-charge of the cell;

said computing means further being operative to produce an oxygen/current signal indicative of the amount of current flow through the cell attributable to the generation of oxygen and to subtract said oxygen/current signal from said total current signal in the course of computing said state-of-charge signal; and display means responsive to said state-of-charge signal for producing a visual display indicative of the state-of-charge of the cell.

2. The coulometer of claim 1 further comprising display means responsive to said state-of-charge signal for producing a visual display indicative of the state-of-charge of the cell.

3. The coulometer of claim 1 wherein said component gas signal is indicative of the fraction of oxygen in the gas generated by the cell.

4. The coulometer of claim 1 wherein said oxygen/current signal is produced in accordance with the rate at which oxygen is produced by the electrolytic cell.

5. The coulometer of claim 3 wherein said total gas flow rate includes an oxygen flow rate and a hydrogen flow rate and wherein said computing means produces an oxygen/current signal indicative of the current flow through the cell attributable to the generation of oxygen and a hydrogen/current signal indicative of the amount of current flow through the cell attributable to the generation of hydrogen and subtracts the oxygen/current and hydrogen/current flow signals from said total current signal to yield said state-of-charge signal.

6. The coulometer of claim 5 wherein said gas measuring means comprises a gas flow meter and an oxygen analyzer and said computing means comprises a programmed computer.

7. The coulometer of claim 2 wherein said gas signal is indicative of the fraction of hydrogen in the gas generated by the cell.

8. The coulometer of claim 7 wherein said computing means produces a hydrogen/current signal indicative of the amount of current flow through the cell attributable to the generation of hydrogen and subtracts said hydrogen/current signal from said total current signal in the course of computing said state-of-charge signal.

9. The coulometer of claim 8 wherein said hydrogen/current signal is produced in accordance with the rate at which hydrogen is produced by the electrolytric cell.

10. A coulometer for measuring the state-of-charge of an open-cell lead/acid battery, said coulometer comprising:
a gas flow meter coupled to a gas vent of the battery;
a gas analyzer coupled to the gas vent of the battery;
computing means responsive to outputs of said gas flow meter and said gas analyzer for producing a state-of-charge signal indicative of the state-of-charge of the battery; and
display means responsive to said state-of-charge meter for visually indicating the state-of-charge of the battery.

11. A method for measuring the state-of-charge of an electrolytic cell having an aqueous electrolyte, comprising the following steps:
measuring the total current flow through the cell;
measuring the rate at which the cell generates gas;
computing the amount of current flow through the battery attributable to the measured rate of gas flow;
computing the difference between the total current flow and the current flow attributable to the generated gas; and
integrating said difference in current flow over a period of time so as to arrive at the state-of-charge of the cell.

12. A coulometer for measuring the state-of-charge of an electrolytic cell having a aqueous electrolyte, said coulometer comprising:

current measuring means for producing a total current signal indicative of the amount of current flow through the cell;
gas measuring means for producing a total gas flow rate signal and at least one component gas signal indicative of the rate of generation of oxygen by the cell;
computing means responsive to said total current signal, said total gas flow rate signal and said component gas signal for producing a state-of-charge signal indicative of the state-of-charge of the cell;
wherein said computing means produces an oxygen/current signal indicative of the current flow through the cell attributable to the generation of oxygen and a hydrogen/current signal indicative of the amount of current flow through the cell attributable to the generation of hydrogen and subtracts the oxygen/current and hydrogen/current flow signals from said total current signal to yield said state-of-charge signal; and
display means responsive to said state-of-charge signal for producing a visual display indicative of the state-of-charge of the cell.

13. The coulometer of claim 12 wherein said gas measuring means comprises a gas flow meter and an oxygen analyzer and said computing means comprises a programmed computer.

14. A coulometer for measuring the state-of-charge of an electrolytic cell having an aqueous electrolyte, said coulometer comprising:
current measuring means for producing a total current signal indicative of the amount of current flow through the cell;
gas measuring means for producing a total gas flow rate signal and at least one component gas signal indicative of the rate of generation of hydrogen by the cell;
computing means responsive to said total current signal, said total gas flow rate signal and said component gas signal for producing a state-of-charge signal indicative of the state-of-charge of the cell;
wherein said computing means produces a hydrogen/current signal indicative of the amount of current flow through the cell attributable to the generation of hydrogen and subtracts said hydrogen/current signal from said total current signal in the course of computing said state-of-charge signal; and
display means responsive to said state-of-charge signal for producing a visual display indicative of the state-of-charge of the cell.

15. The coulometer of claim 14 wherein said hydrogen/current signal is produced in accordance with the rate at which hydrogen is produced by the electrolytic cell.

* * * * *